United States Patent
Yamada et al.

(10) Patent No.: US 10,710,947 B2
(45) Date of Patent: Jul. 14, 2020

(54) METHOD FOR IMPROVING THE MANUFACTURE OF ETHYLENE GLYCOL

(71) Applicant: Scientific Design Company, Inc., Little Ferry, NJ (US)

(72) Inventors: Eunice Yamada, Pittstown, NJ (US); Shaun McGovern, Hoboken, NJ (US); Barry Jay Billig, Irvington, NY (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 16/398,975

(22) Filed: Apr. 30, 2019

(65) Prior Publication Data

US 2019/0330132 A1 Oct. 31, 2019

Related U.S. Application Data

(60) Provisional application No. 62/664,914, filed on Apr. 30, 2018.

(51) Int. Cl.
  *C07C 29/152* (2006.01)
  *C07C 29/10* (2006.01)

(52) U.S. Cl.
  CPC ............ *C07C 29/152* (2013.01); *C07C 29/10* (2013.01)

(58) Field of Classification Search
  CPC ...... C07C 29/10; C07C 29/106; C07C 29/152
  See application file for complete search history.

(56) References Cited

U.S. PATENT DOCUMENTS

| | | |
|---|---|---|
| 3,028,434 A | 4/1962 | Weisz et al. |
| 3,563,914 A | 2/1971 | Wattimena |
| 3,702,259 A | 11/1972 | Nielsen |
| 3,867,113 A | 2/1975 | Foster et al. |
| 3,957,698 A | 5/1976 | Hatch |
| 4,160,116 A | 7/1979 | Mieno et al. |
| 4,165,440 A | 8/1979 | Kim |
| 4,519,875 A | 5/1985 | Becker et al. |
| 4,761,394 A | 8/1988 | Lauritzen |
| 4,766,105 A | 8/1988 | Lauritzen |
| 4,778,567 A | 10/1988 | Kakimoto et al. |
| 4,875,909 A | 10/1989 | Kakimoto et al. |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |

(Continued)

FOREIGN PATENT DOCUMENTS

| | | |
|---|---|---|
| CN | 1208135 A | 2/1999 |
| CN | 103709001 A | 4/2014 |

(Continued)

OTHER PUBLICATIONS

International Search Report dated Aug. 12, 2019, received in International Application No. PCT/US2019/029830.

(Continued)

*Primary Examiner* — Yate' K Cutliff
(74) *Attorney, Agent, or Firm* — Scully Scott Murphy and Presser

(57) ABSTRACT

A method for improving the manufacture of an existing ethylene glycol manufacturing that includes inserting a catalytic hydration reaction section with multiple adiabatic reactors.

11 Claims, 1 Drawing Sheet

(56) References Cited

U.S. PATENT DOCUMENTS

| | | |
|---|---|---|
| 5,187,140 A | 2/1993 | Thorsteinson et al. |
| 5,407,888 A | 4/1995 | Herzog et al. |
| 5,763,691 A | 6/1998 | Kawabe et al. |
| 5,945,568 A | 8/1999 | Nagata et al. |
| 6,160,187 A | 12/2000 | Strickler et al. |
| 6,211,419 B1 | 4/2001 | Strickler et al. |
| 7,453,015 B2 | 11/2008 | Van Kruchten et al. |
| 7,663,005 B2 | 2/2010 | Crudge et al. |
| 7,683,221 B2 | 3/2010 | Powell et al. |
| 8,183,400 B2 | 5/2012 | Szul et al. |
| 8,480,961 B2 * | 7/2013 | Hassan ............ B01F 7/00766 422/129 |
| 2002/0082456 A1 | 6/2002 | Van Kruchten et al. |
| 2005/0119510 A1 * | 6/2005 | Boons .................. C07C 29/106 568/860 |
| 2006/0161026 A1 | 7/2006 | Van Kruchten |
| 2006/0183927 A1 | 8/2006 | Billig et al. |
| 2007/0037991 A1 | 2/2007 | Rizkalla |
| 2017/0298035 A1 | 10/2017 | Olthof |

FOREIGN PATENT DOCUMENTS

| | | |
|---|---|---|
| CN | 104974115 A | 10/2015 |
| EP | 0123700 A1 | 11/1984 |
| EP | 0123709 A1 | 11/1984 |
| EP | 1828086 B1 | 10/2009 |
| EP | 2121646 B1 | 2/2011 |
| JP | 2010528113 A | 8/2010 |
| WO | 0035840 A1 | 6/2000 |
| WO | 2006072766 A1 | 7/2006 |
| WO | 2008150338 A1 | 12/2008 |
| WO | 2009105252 A1 | 8/2009 |
| WO | 2017178418 A1 | 10/2017 |

OTHER PUBLICATIONS

International Search Report dated Aug. 13, 2019, received in International Application No. PCT/US2019/029820.
International Search Report dated Aug. 13, 2019, received in International Application No. PCT/US2019/029818.
International Search Report dated Aug. 16, 2019, received in International Application No. PCT/US2019/029825.
Shvets, V. F., et al., "The Model of Catalytic Reactor of Ethylene Glycol Production", Organic Process Research & Development, Published on web Nov. 2, 2005, pp. 768-773, vol. 9, No. 6.
Othmer, D. F., et al., "Glycol Production—Hydration of Ethylene Oxide", Industrial and Engineering Chemistry, Sep. 1958, pp. 1235-1244, vol. 50, No. 9.
Van Hal, J. W., et al., "Investigation of three types of catalysts for the hydration of ethylene oxide (EO) to monoethylene glycol (MEG)", Catalysis Today, Available online Mar. 19, 2007, pp. 310-315, 123.
Office Action dated Dec. 13, 2019 received in U.S. Appl. No. 16/399,045.

* cited by examiner

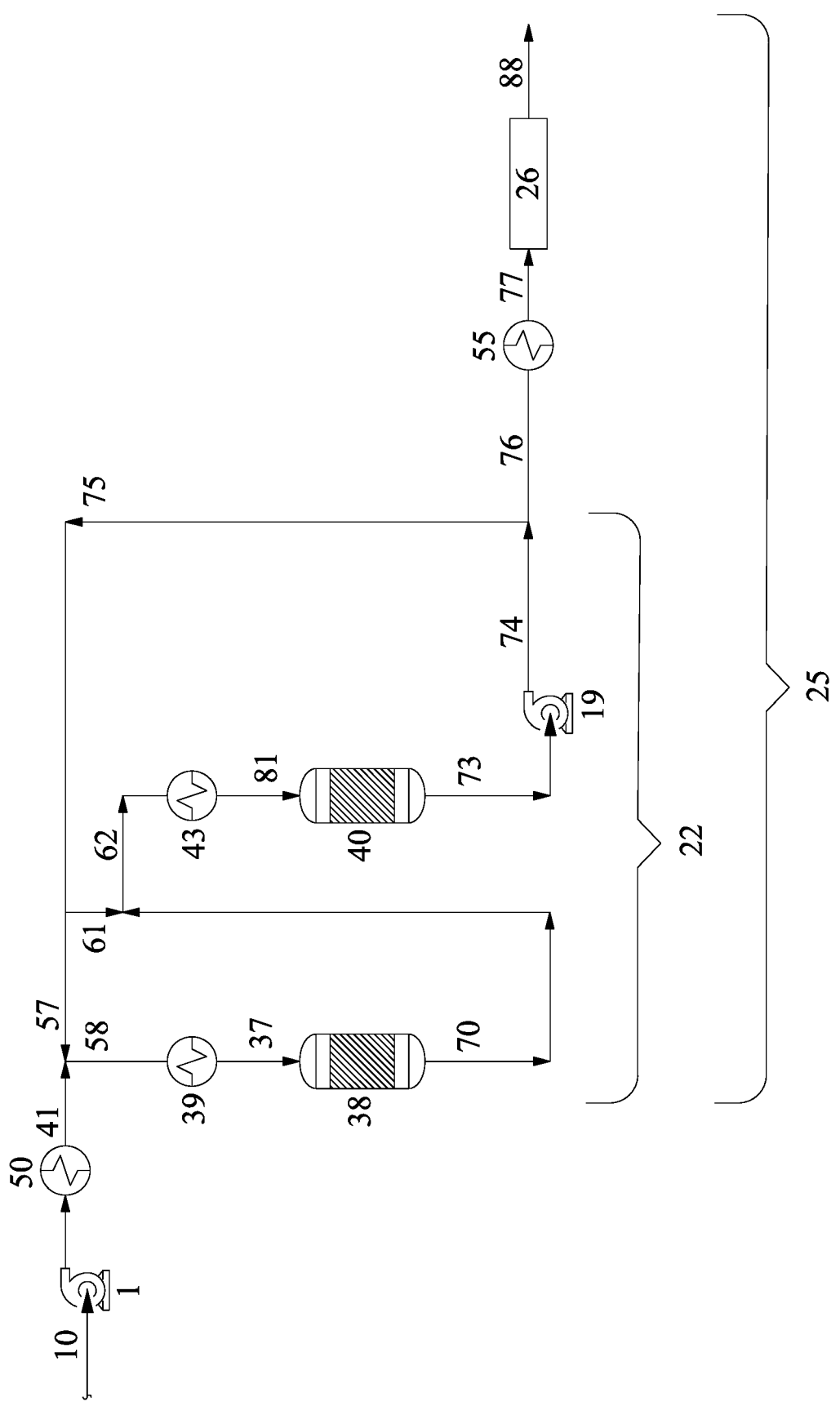

METHOD FOR IMPROVING THE MANUFACTURE OF ETHYLENE GLYCOL

CROSS REFERENCE TO RELATED APPLICATION

The present invention claims the benefit of U.S. Provisional Patent Application No. 62/664,914 filed Apr. 30, 2018, the entire content and disclosure of which is incorporated herein by reference.

FIELD OF THE INVENTION

The present invention relates to a method for the oxidation of ethylene into ethylene oxide and the hydration of ethylene oxide into ethylene glycol.

BACKGROUND OF THE INVENTION

The role of ethylene glycol in society has advanced considerably from the time when shortly after its first synthesis the molecule's properties became the subject of a fierce dispute between two giants of early organic chemistry, Adolphe Wurtz and Hermann Kolbe. In particular, Wurtz and Kolbe disputed ethylene glycol's functionality and chemical formula among the still emerging understanding of alcohol homologs, which were key to Kolbe's greater theories about chemical structure. The laboratory soon became a proxy war of the rising industrial and technical might of the growing rivalry between Germany and France with both countries devoting considerable resources to the scientific investigation and Wurtz's wizardry at chemical synthesis giving France a considerable advantage. The dispute was ended only by resort to arms when Bismarck's German Confederation annexed Wurtz's Alsatian homeland as a result of the Franco-Prussian war and thus, essentially turned an international dispute into a domestic one.

Today, interest in ethylene glycol is more peaceful but all the more competitive because ethylene glycol is one of the most widely produced organic chemicals. Since large scale industrial production of ethylene glycol began on the eve of the First World War, dramatic increases in the use of the internal combustion engine to power automobiles and other vehicles has spurred demand for ethylene glycol as a coolant and antifreeze. Since then, the increase in the production of ethylene glycol has only accelerated, so that by 2017, the estimated worldwide production of ethylene glycol was in excess of 25 billion tons.

Ethylene glycol is typically prepared as one of many of the derivatives of ethylene oxide, and though other production routes are available, most is produced from ethylene oxide in a liquid phase non-catalytic thermal hydration process. Because ethylene oxide reacts with ethylene glycols more readily than it reacts with water it is inevitable that a mixture of monoethylene glycol as well as higher glycol coproducts, such as diethylene glycol, triethylene glycol and yet still higher ethylene glycols will be formed. Although these higher glycols have considerable economic value, many producers and plant operators wish to avoid producing them because the end-user market for these products is not as well developed and it may be difficult to find and distribute these higher glycols to industrial consumers who have a need for them.

In order to suppress the reaction between product glycol and ethylene oxide and thereby reduce the formation of these higher glycols, conventional non-catalytic hydration are performed with an amount of water that far exceeds the stoichiometric amount of water for the hydration of ethylene oxide to ethylene glycol, e.g., 15 to 40 moles of water per mole of ethylene oxide. This addition of excess water is effective at balancing the kinetically-favored competing reaction between product glycol and ethylene oxide, which as mentioned above competes with the hydration of ethylene oxide to monoethylene glycol. However, while effective at suppressing the production of higher ethylene glycols, using a large excess of water relative to ethylene oxide presents a problem for the plant operator in removing these large excesses of unreacted water because such removal is energy intensive and requires large-scale evaporation/distillation facilities. Accordingly, there has been interest in alternatives to thermal hydration of ethylene oxide for the production of ethylene glycol, such as the homogeneous catalytic hydration of ethylene oxide to monoethylene glycol.

The earliest examples of this approach included the homogeneous catalysis of sulfuric acid and their associated salts (see Othmer, D. F. and Thakar, M. S., Glycol Production—Hydration of Ethylene Oxide. Ind. Eng. Chem. 1958, 50, 1235) European Patent No. 0 123 700 described refinements of these earlier generations of acid catalysts by treating them with, e.g., ethylamines to partially neutralize them in the hope of improving the selectivity of the hydration reaction to monoethylene glycol. Since then other salts have been proposed for homogeneous systems, such as quaternary phosphonium salts as described in U.S. Pat. No. 4,160,116 and metallate and bicarbonate salts as described in U.S. Pat. No. 7,683,221. Increasingly creative combinations of organic species such as EDTA and Salen compounds have also been proposed as homogeneous catalysts (see Hal, J. W., Ledford, J. S., and Zhang, X., Catalysis Today 123 (2007), 310-315).

Homogeneous catalyst systems are often utilized in a two-step process for manufacturing ethylene glycol, see e.g., U.S. Pat. No. 4,519,875 in which ethylene oxide is first reacted with carbon dioxide to manufacture ethylene carbonate, which is then hydrolyzed to ethylene glycol, with typically the same catalyst being used in both steps. Following this pioneering patent, continued research has produced incremental refinements in the two-step process. For example, in U.S. Pat. No. 5,763,691, the carbonation reaction is catalyzed in the ethylene oxide absorbate in the presence of a halogenated organic phosphonium salt carbonation catalyst. Additional research has considerably expanded the scope of known catalysts; see for example macrocyclic chelating compounds ("crown ethers") described in U.S. Pat. No. 7,453,015.

While homogeneous catalysts improved the selectivity of towards monoethylene glycol compared to non-catalytic therm hydration, the homogeneous catalyst hydration processes have the drawback of adding considerably more process complexity. In addition to the multi-step, multi-reaction catalytic hydration steps mentioned above, there is yet an additional multiplicity of steps after the reaction has been completed. As just one example: the glycol product solution produced by the reaction contains soluble or suspended homogeneous catalyst. This necessitates an additional step of separating the homogeneous catalyst from the glycol product solution which increases the cost and complexity of the process. The additional complexity of the homogeneous catalyst hydration brings with it the additional flaw that it is neither very versatile nor flexible. In particular the two-step hydration process also lacks the versatility to be used both for new plants and revamps. In order to attain the full benefits of using this two-step process to revamp an existing ethylene glycol plant the entire reaction and evaporation section of the existing plant would have to be removed and replaced by new process sections. Thus, this two-step hydration process can be used only for new, "grass roots" plants and cannot be used for revamps because in the case of revamps it would be necessary to remove and replace the entire "back-end," making such a revamp cost-prohibitive.

Thus, for an existing plant operator seeking to supplement or replace the existing thermal, non-catalytic hydration process with a catalytic process this two-step hydration process will not be suitable. There exists a need in the art for a way for a plant operator to improve the selectivity to monoethylene glycol of an existing non-catalytic, thermal process.

An improved process has been discovered in the present invention for the efficient and selective hydration of ethylene oxide to ethylene glycol. This improved process allows for existing plants using conventional non-catalytic hydration processes to be revamped to incorporate a catalytic hydration process that either replaces or supplements the non-catalytic process with a heterogeneous catalytic hydration process. These heterogeneous catalytic process are considerably easier to operate because they do not require multiple catalysis steps, homogeneous catalyst separation steps and other process steps.

BRIEF SUMMARY OF THE INVENTION

The present invention relates to a method for improving the manufacture of an existing ethylene glycol manufacturing process including supplying a pipe reactor feedstream comprising ethylene oxide and water to a non-catalytic glycol reactor; reacting the ethylene oxide and water in the non-catalytic glycol reactor to produce a product stream; modifying the supply of the pipe reactor stream as follows providing a catalytic hydration feedstream containing ethylene oxide and water; combining the catalytic hydration feedstream with a recirculation split stream to form a first reactor inlet stream; supplying the first reactor inlet stream to an inlet of a first adiabatic reactor, the inlet of the first adiabatic reactor being at a first inlet temperature; reacting the ethylene oxide and water in the presence of a first ion exchange resin catalyst in the first adiabatic reactor to thereby produce an effluent stream containing water, ethylene glycol, and unreacted ethylene oxide; further combining the effluent stream with a recirculation supply stream to form a combined stream containing water, ethylene glycol and unreacted ethylene oxide; supplying the combined stream to an inlet of a second adiabatic reactor, the inlet of the second adiabatic reactor being at a second inlet temperature; reacting ethylene oxide and water in the presence of a second ion exchange resin catalyst in the second adiabatic reactor to thereby produce a second reactor effluent stream containing water, ethylene glycol, and unreacted ethylene oxide; compressing the second reactor effluent stream; dividing the second reactor effluent stream into a recirculation stream and a forward stream; dividing the recirculation stream into the split recirculation stream and the supply recirculation stream; supplying the forward stream as the pipe reactor feedstream to a non-catalytic pipe reactor to produce a product stream wherein the total concentration of DEG, TEG and higher glycols in the product stream is greater than the total concentration of DEG, TEG and higher glycols in the forward stream.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawing:

FIG. 1 is a schematic flow sheet for a process for catalytic hydration of ethylene oxide to ethylene glycol as incorporated in the present invention.

DETAILED DESCRIPTION OF THE INVENTION

All parts, percentages and ratios used herein are expressed by volume unless otherwise specified. All pressures are absolute. All documents cited herein are incorporated by reference.

By "water" it is meant any kind of water suitable for use in chemical and petrochemical processing, including deionized, demineralized, industrial, potable and distilled water. Condensate of steam and condensate obtained from the dehydration and evaporation section of the glycol manufacture process may also be used.

The non-catalytic glycol reactor 26 and catalytic hydration reactors 38 and 40 as prepared according to the present invention as shown in FIG. 1 and will be described in greater detail below.

Ethylene oxide by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 40% of ethylene and from about 3% to about 12% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more reaction moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

For purposes of illustration only, the following are conditions that are often used in current commercial ethylene oxide reactor units: a gas hourly space velocity (GHSV) of 1500-10,000 h$^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The aforementioned reactor effluent exits through the reactor outlet, is cooled and flows to the EO scrubbing column, where the reactor effluent is contacted with recirculated lean cycle water to absorb the ethylene oxide from the reactor effluent. These scrubbing column liquids (rich cycle water) are then fed to the EO stripping column for the recovery of the ethylene oxide. In the EO stripping column, the ethylene oxide is stripped out of the rich cycle water to form a stripper overhead which is vaporous ethylene oxide-water mixture, particular rich in ethylene oxide. Preferably this vaporous stripper overhead contains at least about 80 wt % ethylene oxide, preferably at least about 95 wt % ethylene oxide. The stripper overhead then flows to the lower portion of a second ethylene oxide absorber.

The second ethylene oxide absorber prepares a concentrated aqueous ethylene oxide solution that is suitable to produce purified ethylene oxide or for hydration to ethylene glycol. Cooled process water is introduced to an upper portion of the second ethylene oxide absorber—this water is cooled to increase the concentration of ethylene oxide in the second ethylene oxide absorber bottoms solution. Within the second ethylene oxide absorber, the stripper overhead vapor and the cooled process water are countercurrently contacted to further maximize the concentration of ethylene oxide in the cooled processes water. Preferably, the second ethylene oxide absorber is constructed so as to facilitate this intimate vapor-liquid contact, and any suitable arrangement or configuration that accomplishes this is acceptable. It is preferred that substantially all, meaning at least about 95 mol %, preferably at least about 99 mol % of the ethylene oxide that is supplied to the second ethylene oxide absorber 84 as part of the stripper overhead is reabsorbed into the cooling water to produce an ethylene oxide-water solution. By so absorbing substantially all of the ethylene oxide little or (preferably) no ethylene oxide is present in the second ethylene oxide absorber overhead meaning that not only is there no emission of ethylene oxide into the atmosphere (which is prohibited by emission and environmental regulations) but also the plant operator is not forced to introduce excess process complications to handle and recycle or dispose (e.g., incinerate) any "excess" vaporous ethylene oxide.

Having thus been so designed and operated as discussed above and with substantially all of the ethylene oxide having been absorbed into the ethylene oxide-water solution then the ethylene oxide-water solution in the bottom of the second ethylene oxide absorber is concentrated in ethylene oxide to contain at least about 5 mol %, preferably at least about 10 mol % ethylene oxide, with the balance being mostly water as well as trace amounts of dissolved carbon dioxide, unreacted ethylene oxide and possibly other impurities. The ethylene oxide-water solution thus formed is withdrawn from the bottom of the second ethylene oxide absorber and are pumped to the light ends columns. The vapors not absorbed into the cooled process water pass out of the second ethylene oxide absorber through the second ethylene oxide absorber overhead that contains most of the carbon dioxide that was present in the second ethylene oxide absorber as well as other non-condensable light gas components (especially, e.g., ethylene, oxygen, and inert gases). The second ethylene oxide absorber overhead can then be vented, treated, disposed of, or in the case of e.g., ethylene possibly recovered and recycled for further use.

The trace amounts of vaporous carbon dioxide, unreacted ethylene oxide, and other impurities in the ethylene oxide-water may then be stripped out in the light ends column. These vaporous components pass out of the light ends overhead. The light ends column removes these impurities prior to the conventional products section which includes a purification column, a non-catalytic glycol reactor, or both. The bottoms of the light ends columns are an aqueous ethylene oxide solution, the solution being divided by the baffle between a right and left side, with the left side bottoms stream being a purification column feed stream pumped to the purification column and the right side bottoms stream, the glycol reactor feed stream pumped to heat exchanger where it is heated to a temperature of about 130° C. to about 160° C. and the resulting pipe reactor stream is supplied to the glycol reactor 26. This glycol reactor 26 is a conventional non-catalytic pipe reactor for the thermal conversion of ethylene oxide and water to an ethylene glycol stream.

In the purification column an overhead purified ethylene oxide stream is produced. This stream may be stored under appropriate handling conditions for later use or may be immediately processed into ethylene oxide derivatives such as ethoxylates, ethanolamines, glycol ethers and other chemical products. The purification column bottoms are sent for reuse elsewhere in the process.

In the present invention the conventional products section for making both purified ethylene oxide and ethylene glycol can be replaced by catalytic hydration system. By "replacing" or "replaced" it is meant that the non-catalytic glycol reactor and/or purification column are taken off-line at least temporarily and the feed stream directed instead to the catalytic hydration reaction section 25.

Rather than replaced, the catalytic hydration section 25 can be "inserted" into the process scheme. As shown in FIG. 1 the glycol reactor 26 is still used but the catalyst hydration feedstream 10 from the bottoms of the light end column is first sent to the catalytic hydration section.

By replacing it is not meant that the non-catalytic glycol reactor is permanently replaced with a catalytic hydration reaction section. Rather, the present invention provides sufficient flexibility to replace the non-catalytic glycol reactor with the catalytic hydration reaction section when the plant operator wishes to do so.

In this mode, the catalytic hydration feedstream flows through conduit 10 and is subsequently pressurized further in pump 1, further heated in heat exchanger 50 and travels at elevated pressure into the reaction section 25 as shown in FIG. 1. In the present invention the reaction section contains two or more reactors. In FIG. 1 a reaction section 25 is shown with a train of two catalytic reactors arranged in series configuration with each separated by a heat exchanger. Specifically, the reactor section 25 shows a reactor train of two down-flow, fixed-bed, series-arranged adiabatic reactors, 38 and 40, with inter-stage, on-line heat exchangers 39 and 43 as cooling means. The reactors are designated as the first adiabatic reactor 38 and the second adiabatic reactor 40 but as used herein these adiabatic reactors 38 and 40 may also be referred to as "reactors".

As discussed above, such inter-stage cooling is necessary because the reaction of water with ethylene oxide is highly exothermic, so is it necessary to remove the heat of reaction from the product or outlet streams when the reaction occurs in adiabatic reactor as in the present invention. This differs from isothermal conditions where the heat of reaction is removed directly from the reactor. Maintaining the ion exchange resin catalyst at temperatures that the resin can tolerate is of course critical to reduce swelling, prevent degradation and maximize catalyst life. If operated properly the adiabatic temperature rise can be controlled to a level which maintains both good performance and life.

Lastly, positioned down-stream of the reactor train 22 is a conventional non-catalytic pipe reactor 26 (this reactor of course contains no catalyst).

As mentioned above the ethylene oxide-water solution in conduit 10 is pressurized in pump 1. The ethylene oxide-water solution having been made from the cooled process stream supplied to the second ethylene oxide absorber is relatively cold and thus, must be passed through heat exchanger 50 in order to bring stream 41 to a temperature sufficiently high to drive the hydration reaction of ethylene oxide so that the conversion of ethylene oxide to monoethylene glycol. Thus, heat exchanger brings the temperature of the ethylene oxide-water solution to a temperature of between 70° C. and 100° C.

As mentioned above the ethylene oxide-water solution will comprise preferably about 5 mol % ethylene oxide to about 10 mol % ethylene oxide. Thus the ethylene oxide-water solution contains a significant stoichiometric excess of water to ethylene oxide than is necessary for the hydration of ethylene oxide to ethylene glycol. In molar ratio terms the ethylene oxide-water solution will have a molar ratio of water:ethylene oxide mole ratio of about 5:1 to about 15:1, preferably about 7:1 to about 12:1; and while this represents the aforementioned stoichiometric excess, as mentioned above, it is considerably lower than amounts used in the prior art for non-catalytic hydration. And thus, because the feedstream contains less water, the final product will also have correspondingly lower amounts of water that need to be removed from the product, as described below.

The heated catalytic hydration stream 41 is now supplied to the aforementioned reactor train 22 where it is combined with the recirculated split stream 57 to form a first reactor feed stream 58. As the recirculation split stream 57 is considerably depleted in ethylene oxide compared to the ethylene oxide-water solution stream 41 supplied to the reaction train the resulting first reactor feed stream 58 will have a higher ratio of water to ethylene oxide compared to the ratio of water to ethylene oxide in the ethylene oxide-water solution stream 41, preferably a molar ratio of 40:1 to about 10:1, preferably about 30:1 to about 20:1, water:ethylene oxide. This is in the case with the successive reactor illustrated in FIG. 1, as the amount of ethylene oxide is gradually depleted as more and more monoethylene glycol is made and the ratio of water to ethylene oxide in successive reactors increases. This is a considerable improvement over conventional operation of catalytic and non-catalytic hydration. By recirculating a portion of the reactor effluent from the second reactor (streams 57 and 61 via stream 75), a high water:ethylene oxide ratio in the feedstream to each reactor can be obtained while simultaneously maintaining a lower overall water rate in the product stream 88 at the end of the reactor system which is fed to the evaporators for water removal. Thus, the reaction of ethylene oxide and water is catalyzed both by the presence of ion exchange resin and the significant excess of water to ethylene oxide. This encourages monoethylene glycol production and suppression of higher glycol homolog formation—there is thus a benefit of both effects. And yet this is maintained while having a final product that is much more concentrated in ethylene glycol and thus requires far less energy in the evaporation section. For example in the present invention the final product of the reactor section, the combined reactor product 88, may have a total glycols (mono-, di-, tri- and trace higher) concentration of 16 wt % or even higher while by contrast in a conventional plant the glycol reactor effluent sent to the evaporation section has a total glycols concentration of about 12 wt %, thus reducing the amount of heat duty necessary for evaporation of the excess water has been reduced by a factor of at least 25%.

As mentioned above streams, 41 and 57 are combined and cooled in heat exchanger 39 to form the feedstream 37 to the first reactor 38 and thus, the temperature of reactor 38 is regulated by controlling the temperature of stream 37, while the temperature in the successive series reactor 40 is each regulated with the use of exchanger 43.

Regulating temperature and pressure are important parts of the process of the present invention. The hydration reaction in the present invention is carried out as a liquid phase process. In the present invention by "liquid phase process" it is meant that the feedstreams supplied to the reactor, the reactor product or reactor effluent streams, and the reactants inside the reactor are maintained in the liquid phase. Accordingly, the temperature and pressure in each reactor is such that as the streams are supplied to and enter into each reactor, they are maintained in the liquid phase. The temperature and pressure in each reactor is thus regulated to maintain the contents of the reactor in a liquid phase. The choice of temperature is largely determined by the considerations of the aforementioned paragraphs. Thus given the temperature ranges, below, in the present invention with the reactor contents being in liquid form, the pressure will be between about 7 atm to about 15 atm, preferably about 10 atm to about 13 atm.

In selecting the temperature two competing requirements must be balanced. First, as mentioned above the temperature of the inlet in the present invention must be sufficiently high to drive the hydration reaction of ethylene oxide so that there is significant conversion of ethylene oxide to monoethylene glycol. In the present invention the conversion percentage of ethylene oxide to monoethyelene glycol in the first reactor should be at least about 50%, preferably at least about 70% of the total ethylene oxide reacted. Thus, the temperature at the inlet to reactor 38 must be within the range of about 50° C. to about 90° C., preferably within the range of about 70° C. to about 85° C. The conversion percentage of ethylene oxide to monoethyelene glycol in the second reactor 40 should be about at least 10% of the total EO reacted, preferably at least about 20% of the total EO reacted. Thus, the temperature at the inlet to reactor 5 must be within the range of about 70° C. to about 110° C., preferably within the range of about 80° C. to about 95° C. However, the temperature in the reactor (and consequently at the reactor outlet) should not be too high because, as mentioned above, a significantly high temperature increase inside the reactor causes swelling and degradation of the ion exchange resin. High temperatures in the reactor are the result of the exothermic hydration reaction and so to moderate any temperature increase this heat of reaction must be removed. In prior art isothermal operations the heat of reaction can be removed, e.g., by absorption into a shell-side coolant. This is not possible with the adiabatic reactors of the present invention, which have considerably less process complication but are correspondingly less versatile in their heat removal capacities. However, in the present invention it has been discovered that the temperature rise can nonetheless be at least partially moderated within a range suitable for stable operation of the ion exchange resin catalyst by the superabundant water in each reactor which acts as a heat sink. Thus, while one goal of the present invention is to reduce the amount of water used in the production of ethylene glycol, nonetheless at least a minimum amount of water is necessary to moderate the temperature increase in the reactors arising from the exothermic reaction. As described above, both of these goals are met in the present invention by recirculating portions of stream 75 to the same reactor 38 and 40. With this inventive configuration a progressively higher water:ethylene oxide ratio is obtained inside successive reactors moderating the exotherm so that at the outlet of each reactor the temperature is between about 90° C. to about 120° C., preferably between about 95° C. to about 110° C.

Despite the success of the present invention at moderating the temperature rise in the reactor it may nonetheless be necessary to reduce the reactor effluent temperature still further until reaching the acceptable inlet temperature range mentioned above. In order to do this the streams 58 and 62, including their respective recirculation streams 57 and 61, are passed through heat exchangers 39 and 43, respectively This presents an opportunity for heat integration as a flow stream (not pictured) from outside the reaction section may be heated in any of the heat exchangers by indirect heat exchange with the reactor effluent from one or more of the series reactors.

As noted above, at higher temperatures there is nearly complete conversion of ethylene oxide to monoethylene glycol—at lower inlet temperatures not all of the ethylene glycol will react and detectable amounts of ethylene oxide will appear and remained unreacted ("break through") in the reactor effluent. In certain situations it may be desired to reduce the inlet temperature in order to reduce the ethylene oxide conversion to allow for more ethylene oxide breakthrough—when for example it is desired to extend the life of the ion exchange resin catalyst or in other situations, as described below.

In addition to the above-mentioned parameters and operating conditions, other factors that may be considered when operating the process include but are not limited to: reactor and process configuration, the conversion rate and selectivity of the ion exchange resin catalyst, and reactants flow rate (LHSV).

With the aforesaid considerations in mind, feed stream 41, having been heated to an appropriate temperature in heat exchanger 50, combines with the recirculation split stream 57 to form the first reactor feed stream 58 after being cooled to a sufficient reaction temperature in heat exchanger 39, enters reactor 38 where the ethylene oxide reacts with water in the presence of an ion exchange resin catalyst or catalyst bed to form monoethylene glycol. In the adiabatic reactors of the present invention, e.g., reactor 38, mixing ethylene oxide with excess water at or above the catalytic temperature in the presence of the catalyst results in the hydration of ethylene oxide that is highly selective to monoethylene glycol so that at least about 95%, preferably at least about 98% of the ethylene oxide that is converted is converted to monoethylene glycol with only small percentages being converted into higher glycols like diethylene glycol or triethylene glycol (conversion percentages are mentioned above). In addition to the monoethylene glycol product, each effluent of the reactors in the present invention contains water and ethylene oxide (the excess amounts available for recirculation to the same reactor or for further addition into the next reactor), and trace quantities of other components including ethylene oxide and higher glycol homologs.

Leaving reactor 38, effluent stream 70 is combined with recirculated supply stream 61 in a volume ratio of stream 70: stream 61 is about 0.5:1 to about 2:1. The combination stream 62 is then passed through heat exchanger 43, and the cooled stream 81 feeds reactor 40. In reactor 40 and as in reactor 38 the ethylene oxide reacts with water at a high selectivity and conversion rate so that the second reactor effluent stream 73 contains like the first reactor effluent contains unreacted water and ethylene oxide as well as monoethylene glycol and the trace components mentioned above. The effluent from reactor 40, is pumped in pump 19 and is subsequently divided between a forward stream 76 and a recirculation stream 75, which itself is subsequently divided into recirculation split stream 57 and recirculation supply stream 61 to reactors 38 and 40, respectively. Essentially the only difference between the first reactor effluent 70 and the second reactor effluent 73 is that the latter contains more monoethylene glycol because it contains the amount of monoethylene glycol that is produced in both reactors 38 and 40 and accordingly contains significantly less ethylene oxide.

The recirculation split stream 57 and recirculation supply stream 61 are each combined with the fresh feed stream 41 and reactor 38 effluent stream 70 respectively. The combined feedstream to reactors 38 and 40 passed through heat exchangers 39 and 43 respectively to ensure the feed streams are at target temperatures.

In addition to the previously described reactors train encompassing the two down-flow, fixed-bed series reactors, the reactors train also includes a conventional pipe reactor 26 to which the forward reactor effluent 76 may be supplied. In the present invention this pipe reactor 26 is configured and operated to provide hitherto unknown levels of versatility and operability to a catalytic hydration process scheme, which shall now be described in more detail.

First, in addition to increasing the conversion and selectivity of the reaction of ethylene oxide and water to MEG, the present invention may also be operated and configured to increase the versatility and adaptability of the hydration process by allowing the process operator to make di- and triethylene glycol. This can be done by physically bypassing one or more of the catalytic reactors 38 or 40 (this bypass itself is not illustrated) and thereby removing the one or more catalytic reactors from the circulation of the feedstream. The ethylene oxide that "breaks through" that remains unreacted after by-passing one or more of the aforementioned catalyst reactors is sent to the non-catalytic pipe reactor 26 for thermal conversion of ethylene oxide and water to ethylene glycol. As the pipe reactor 26 is non-catalytic and relies entirely on thermal conversion the forward catalytic reactor effluent 76 is preheated in heat exchanger 55 to arrive at pipe reactor stream 77 within the effective temperature range for non-catalytic hydration of ethylene oxide into monoethyelene glycol—preferably the inlet temperature of the pipe reactor 26 is from about 130° C. to about 160° C.

Of course this non-catalytic thermal conversion is significantly less selective to MEG, with substantial amounts of higher glycols such as DEG and TEG also produced so that by increasing the amount of ethylene oxide that is converted into ethylene glycol in the pipe reactor, the reactor product 88 contains less MEG and more DEG and TEG than would be produced if only the catalytic reactors were being used. Thus, the reactor product 88 has a higher total concentration of DEG, TEG and higher glycols than the total concentration of DEG, TEG and higher glycols in the forward stream 76. This provides the operator a versatile and flexible process for ethylene glycol production as the output of mono-, di- and triethylene glycol product may be adjusted by the operator to meet demand. In a limiting case, all two series reactors are bypassed so that only the final non-catalytic pipe reactor 26 is left and all hydration will occur in this reactor—thus converting the catalytic process into a non-catalytic one.

Alternatively, rather than physically bypassing the reactors, a "temperature bypass" can be effected by reducing the inlet temperature to one or more of the catalytic reactors as low as desired to reduce the reaction between the ethylene oxide and water and reducing the amount of monoethylene glycol made in the catalytic reactors, meaning more unreacted ethylene oxide "breakthrough" is seen in the outlets of the catalytic reactors. This ethylene oxide is then converted to ethylene glycol in the pipe reactor as set forth above.

The pipe reactor 26 normally functions as a "finishing" role. When the train of catalytic reactors is operating within normal catalytic efficiency as designed to maximize the conversion of ethylene oxide to ethylene glycol, a small amount of unreacted ethylene oxide will remain unreacted through both catalytic reactors and this ethylene oxide will "breakthrough" in the forward reactor effluent 76. In the present invention the reactor train is preferably operated so that the concentration of ethylene oxide in the forward reactor effluent 76 will be no greater than about 1 mol %. This remaining ethylene oxide can then be converted to monoethylene glycol in the pipe reactor 26. The use of the pipe reactor as a finishing reactor can have significant economic benefit by reducing the required quantity of catalyst. The small conversion of ethylene oxide achieved in the pipe reactor is done at very high excess of water, such that the selectivity to monoethylene glycol over higher glycols is very close to that of the catalytic reactors. The required catalyst quantity and catalytic reactor volume is therefore greatly reduced, while still maintaining a very high overall selectivity to monoethylene glycol Finally, the pipe reactor 26 can also be used as a stand-by reactor in situations where one or more of the catalytic reactors malfunctions or has to be otherwise removed from service because of exhaustion, a blockage in the resin bed or nozzle or some other difficulty commonly observed in operation of ion exchange resin beds. When this happens the malfunctioning catalytic reactor must be taken out of service. This means that there will be excess unconverted ethylene oxide in the catalytic reaction train which is undesirable. This excess ethylene oxide breakthrough can be converted into ethylene glycol in the pipe reactor. Thus, the presence of the pipe reactor 26 in the present prevention provides considerable flexibility and operability for the process operator. Unlike in the prior art where the inability to replace or repair the ion exchange resin catalyst or reactor is a serious disadvantage of solid/heterogeneous catalytic systems, in the present invention reactors may be taken offline for such repair without interrupting operation.

While two reactors and two heat exchangers are shown in the catalytic reactor train, this is for purposes of illustration only. More reactors may be used depending on specific needs and requirements. Increasing the number of reactors has the advantage of reducing the exotherm across each reactor—thus moderating the amount of temperature-induced irreversible swelling the ion exchange resin catalyst experiences inside each reactor. Additionally, increasing the number of reactors also increases the dilution of the ethylene oxide, and because ethylene oxide degrades most ion exchange resins increased dilution is expected to extend resin life.

The primary drawbacks of more reactors is cost and complexity including the additional capital cost of reactors, pumps, exchangers and other equipment as well as the operating costs of larger volumes of ion exchange resin catalyst as well as additional piping, instrumentation and operational complexity.

The alkylene glycol in the reactor product 88 can then be recovered by a multi-effect evaporator or vacuum distillation, or any other suitable means known to those skilled in the art. Recovery techniques can be combined for different stages in the recovery. For example, the multi-effect evaporator can be used to remove water from the reactor effluent while vacuum distillation can be used for glycol drying. Indeed, it is one of the benefits of the present invention that in the post-glycol reaction section of the plant, complexity can be reduced because the amount of heat duty necessary for evaporation of the excess water has been reduced as noted above and as detailed in the example, below. Thus, while prior art plants often incorporate evaporation systems having several effects or stages (see e.g., EP No. 2121646 B1) the present invention requires fewer number of stages.

As discussed above, the present invention may involve one or more ion exchange resin catalysts. Ion exchange resins have a polymer matrix which contain on the surface ion exchanging sites populated by ionic functional groups. Ion exchange resins are typically differentiated between cationic or anionic exchange resin, although other types of ion exchange resins are also available. For a more comprehensive description of cation- and anion-exchange resins see, de Dardel, F. and Arden, T. V. *Ion Exchangers* in *Ullman's Encyclopedia of Industrial Chemistry* (2005).

Suitable polymer matrices for the ion exchange resin catalysts include a polystyrene matrix, a polyacrylic matrix, a polyalkylamine resin as well as other polymeric materials. Preferably, the polymer matrix is cross-linked with divenylbenzene to a sufficient degree to increase the operating capacity while also not increasing the density of the ion exchange material to such an extent that the ion exchange material becomes too physically hard and too chemically resistant to chemical treatment. Preferably the matrix is a styrene, divenylbenzene co-polymer.

Fixed to sites on the polymer matrices described above are ionic stationary groups that determine whether the resin functions as a cationic or anionic ion exchange resin. In solutions, the positive or negative charge of the stationary groups is compensated for by ions of opposite charge which are referred to herein as the functional group.

Strongly acidic cationic ion exchange resins typically include sulfonic groups as stationary groups in turn attached to a styrene-divenylbenzene polymer matrix. Examples of strongly acidic sulfonic cation-exchange resins include Amberlite IR 120, Dowex HCR, Lewatit S 100, and Amberlyst 15, among others.

Cationic ion exchange resins may also include the resin material that is the copolymer obtained by the addition polymerization of an acrylic or methacrylic acid and divinylbeneze such as disclosed in U.S. Pat. No. 3,957,698. Other suitable polymer materials for cationic exchange resins include the resin matrix formed when polyvinylpyridine resin cross-linked with divenylbenzene. Such materials are available under the Reillex HPQ trademark. Sulfonated phenolic polymer resins are also suitable cationic ion exchange resins.

Weakly acidic cationic ion exchange resins typically include carboxylic groups as stationary groups. Examples of weakly acidic cation-exchange resins include Amberlite IRC 86, Dowex Mac-3, Lewatit CNP, among others.

As used herein in the present invention, strongly basic anionic exchange resins contain quaternary ammonium stationary groups. These are further divided into Type I, made by the reaction of trimethylamine with the styrene-divenylbenzene copolymer after chloromethylation, and Type II obtained by the reaction of the styrene-divenylbenzene copolymer with dimethylethanolamine. Suitable examples of such Type I resins include Lewatit M 500 available from Lanxess, and Amberlyst 26 and Amberlite IRA 402, and IRA 410 available from Dow. Suitable examples of strongly basic Type II resins include, e.g., Purolite A510S (Purolite Corporation).

Weakly basic anion exchange resins typically include polyacryclic resins provided with stationary groups by reaction with a polyfunctional amine to result in anion exchange resins such as the tertiary ammonium weakly basic Amberlite IRA 67 and Amberlyst 21 resins (available from Dow). It should be especially noted that this ion exchange resin can be then be further treated with chloromethane or dimethyl sulfate to give a quaternary amine strongly basic Type I resin Amberlite IRA 458 resin (Dow). Weakly basic anion exchange resins may also include a free base group as the stationary group such as the Amberlite IRA-67 resin (Dow).

In a particular embodiment of the present invention the strongly basic anionic exchange resin contains a "linking" group of 3-7 linking atoms, preferably 3-5 carbon atoms between the quaternary ammonium stationary group and the benzene group of the polymer matrix/material. An example of such a linking chain in a strong base resin is illustrated in U.S. Pat. No. 5,945,568 and was produced under the name Diaion TSA1200 (Mitsubishi Chemical). As specified in the '568 patent the linking group which links the quaternary ammonium stationary group to the benzene group of the polymer matrix is not particularly limited as long as it is sufficiently long. Suitable examples of the linking group are an alkylene group or an alkyleneoxyalkylene group. A preferred example for use in the present invention is an anion exchange resin which comprises, as the substrate, a polymer of a vinyl aromatic compound and which has a structure such that a quaternary ammonium group is bonded to the aromatic group via a linking group having a chain length of at least 3.

Without being limited by theory it is believed that in the present invention this linking group prevents the nucleophilic attack on the ammonium stationary group from the benzene ring which otherwise would lead to accelerated deactivation and degradation of the ion exchange resin catalyst and reduced stability and catalyst life.

A variety of ions are suitable for use as the functional group in anionic resins of the present invention and may be selected from the group including bicarbonate, carbonate, hydroxide, bisulfite, carboxylate, citrate, and metalate, and molybdate anions. These functional groups may be used with any of the stationary groups and resin material identified above.

In the present invention it is preferred that the ion exchange resin catalyst is from the group of type I strongly basic anion exchange resins, more preferably type I strongly basic anion exchange resins with a bicarbonate or monocitrate functional group, and most preferably type I strongly basic anion exchange resins with a bicarbonate or monocitrate functional group with a linking group.

In addition to the ion exchange materials specified above, any other suitable cationic or anionic exchange resin may be used such as the cation- and anion-exchange resins set forth above in de Dardel, F. and Arden, T. V. 2008, *Ion Exchanger*, in *Ullman's Encyclopedia of Industrial Chemistry*.

In addition to the aforementioned ion exchange material it is also possible to use a combination of a homoegeneous and heterogeneous catalyst—for example a solid catalyst on which is adsorbed a soluble metallic catalyst. In this case, first a solid catalyst having a metallic catalyst adsorbed on it is prepared. Then, during the liquid-phase hydration reaction described above, the metallic catalyst is desorbed from the solid catalyst and can effectively catalyze the reaction. The metallic catalyst must then be separated from the reaction products and can be reused for re-adsorbing on to the solid catalyst. The solid catalyst in this case can be an ion exchange resin.

The above paragraphs concern the selection of suitable ion exchange resin catalysts for use in the catalytic reactors of the present invention. With respect to the operation of the ion exchange resin-containing catalytic reactors, in FIGS. 2 and 3 the feedstream travels in a direction from the top of the reactor downwards through each of the reactors. This is referred to as "down-flow" mode, but in the present invention the reactors may be operated in either "down-flow" or "up-flow" modes. Down-flow mode processes have the advantage of increasing the density or volume of catalyst within the reactor and thereby reducing the size and cost of the reactors themselves. Down-flow operation also minimize the non-catalytic reaction of water and ethylene oxide to ethylene glycol. However, during the course of down-flow operation catalyst selectivity may be impaired both by local inhomogeneities and impurities that may develop and become entrapped in the catalyst bed and by "channeling" that develops in the catalyst bed.

As can probably be surmised, in up-flow operation the feedstream travels in a direction from the bottom of the reactor upwards. In PCT Publication No. WO2008/150338A1 increased stability and operational life of ion exchange resin in up-flow operational mode was reported. In the present invention with liquid-phase reactants and a solid catalyst up-flow operation may provide a modest amount of bed fluidization during up-flow operation which increases the void fraction between adjacent resin particles allowing for the reduction of the inhomogeneities and contaminates that otherwise become embedded and trapped in the catalyst bed during down-flow operation and degrade catalyst performance. U.S. Pat. No. 6,160,187 has previously disparaged up-flow operation of catalytic reactors because the resulting bed fluidization purportedly causes greater catalyst attrition and reduced monoethylene glycol selectivity due to axial mixing. However, it has been discovered in the present invention that in the liquid phase process of the present invention these criticisms are not realistic because they are more likely to occur in gas/solid catalyst systems where there are much higher velocities, a greater difference in densities (between the gas reactant and solid catalyst compared to a liquid reactant and solid catalyst), and thus a much greater bed expansion than in the present liquid/solid catalyst system of our invention. Thus, up-flow operation remains a suitable mode of operation in the present invention.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 h$^{-1}$, a reactor inlet pressure of 1 Mpa to 3 MPa, a coolant temperature of 180-315° C., an oxygen conversion level of 10-60%, and an EO production rate (work rate) of 100-350 kg EO/m$^3$ catalyst/hr and a change in ethylene oxide concentration, ΔEO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

It will be appreciated by those skilled in the art that changes could be made to the embodiments of the liquid phase process described above without departing from the broad inventive concept thereof. It is understood therefore that this invention is not limited to the particular embodiments or configurations or compositions disclosed, but it is intended to cover modifications within the spirit and scope of the present invention as defined by the appended claims.

We claim:

1. A method for improving the manufacture of an existing ethylene glycol manufacturing process comprising:
   (a) supplying a pipe reactor feedstream comprising ethylene oxide and water to a non-catalytic glycol reactor;
   (b) reacting the ethylene oxide and water in the non-catalytic glycol reactor to produce a product stream;
   (c) modifying the supply of the pipe reactor feedstream as follows:
       providing a catalytic hydration feedstream containing ethylene oxide and water;
       combining the catalytic hydration feedstream with a recirculation split stream to form a first reactor inlet stream;
       supplying the first reactor inlet stream to an inlet of a first adiabatic reactor, the inlet of the first adiabatic reactor being at a first inlet temperature;
       reacting the ethylene oxide and water contained in the first reactor inlet stream in the presence of a first ion exchange resin catalyst in the first adiabatic reactor to produce an effluent stream containing water, ethylene glycol, and unreacted ethylene oxide;
       further combining the effluent stream with a recirculation supply stream to form a combined stream containing water, ethylene glycol and unreacted ethylene oxide;
       supplying the combined stream to an inlet of a second adiabatic reactor, the inlet of the second adiabatic reactor being at a second inlet temperature;
       reacting ethylene oxide and water contained in the combined stream in the presence of a second ion exchange resin catalyst in the second adiabatic reactor to produce a second reactor effluent stream containing water, ethylene glycol, and unreacted ethylene oxide;
       compressing the second reactor effluent stream;
       dividing the second reactor effluent stream into a recirculation stream and a forward stream;
       dividing the recirculation stream into the split recirculation stream and the supply recirculation stream; and
       supplying the forward stream as the pipe reactor feedstream to a non-catalytic pipe reactor to produce a product stream wherein a total concentration of diethyelene glycol (DEG), triethylene glycol (TEG) and higher glycols in the product stream is greater than the total concentration of DEG, TEG and higher glycols in the forward stream.

2. The method according to claim 1, wherein the non-catalytic pipe reactor has an inlet temperature from about 130° C. to about 160° C.

3. The method according to claim 1, wherein each of the first inlet temperature and the second inlet temperature is about 50° C. to about 90° C.

4. The method according to claim 1, wherein each of the first adiabatic reactor and the second adiabatic reactor has an outlet temperature from about 90° C. to about 120° C.

5. The method according to claim 1, wherein a molar ratio of water:ethylene oxide in the first reactor inlet stream is about 40:1 to about 10:1.

6. The method according to claim 5, wherein said molar ratio of water:ethylene oxide is about 30:1 to about 20:1.

7. The method according to claim 1, conducted continuously.

8. The method according to claim 1, wherein a total molar ratio of water:ethylene oxide in the pipe reactor feedstream is about 5:1 to about 15:1.

9. The method according to claim 8, wherein said total molar ratio is about 7:1 to about 12:1.

10. The method according to claim 1, wherein the concentration of ethylene oxide in the forward stream is no greater than about 1 mol %.

11. The method according to claim 1, wherein a conversion percentage of ethylene oxide to monoethyelene glycol in the first adiabatic reactor is at least about 50%.

* * * * *